United States Patent
Singh et al.

(10) Patent No.: US 12,065,414 B2
(45) Date of Patent: Aug. 20, 2024

(54) PROCESS FOR PREPARATION OF ISOXAZOLINE SUBSTITUTED BENZAMIDE COMPOUND

(71) Applicant: CADILA HEALTHCARE LIMITED, Gujarat (IN)

(72) Inventors: Kumar Kamlesh Singh, Gujarat (IN); Sanjay Jagdish Desai, Gujarat (IN); Kuldeep Natwarlal Jain, Gujarat (IN); Jitesh Amratlal Desai, Gujarat (IN); Sarvil Dhirajbhai Patel, Gujarat (IN)

(73) Assignee: ZYDUS LIFESCIENCES LIMITED, Gujarat (IN)

( * ) Notice: Subject to any disclaimer, the term of this patent is extended or adjusted under 35 U.S.C. 154(b) by 0 days.

(21) Appl. No.: 17/465,197

(22) Filed: Sep. 2, 2021

(65) Prior Publication Data

US 2022/0064130 A1   Mar. 3, 2022

(30) Foreign Application Priority Data

Sep. 3, 2020   (IN) .............................. 202021037955

(51) Int. Cl.
*C07D 261/04* (2006.01)

(52) U.S. Cl.
CPC ................................. *C07D 261/04* (2013.01)

(58) Field of Classification Search
CPC ...................................................... C07D 261/04
See application file for complete search history.

(56) References Cited

U.S. PATENT DOCUMENTS 8,952,175 B2 *   2/2015   Yaosaka ................... C07C 65/40
                                                            548/240

* cited by examiner

*Primary Examiner* — Shawquia Jackson
(74) *Attorney, Agent, or Firm* — Nixon & Vanderhye P.C.

(57) ABSTRACT

The invention relates to process for the preparation of isoxazoline-substituted benzamide compound and intermediates thereof. The invention also relates to process for the preparation of Fluralaner and intermediates thereof.

6 Claims, No Drawings

PROCESS FOR PREPARATION OF ISOXAZOLINE SUBSTITUTED BENZAMIDE COMPOUND

This application claims priority to IN Patent Application No. 202021037955 filed 3 Sep. 2020, the entire contents of which is hereby incorporated by reference.

FIELD OF THE INVENTION

The invention relates to process for the preparation of isoxazoline-substituted benzamide compound and intermediates thereof. In particular, the invention relates to process for the preparation of Fluralaner and intermediates thereof.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Isoxazoline-substituted benzamide compound, 4-[5-(3,5-Dichlorophenyl)-4,5-dihydro-5-(trifluoromethyl)-3-isoxazolyl]-2-methyl-N-[2-oxo-2-[(2,2,2-trifluoro ethyl)amino] ethyl]benzamide also known as Fluralaner has structural formula as represented by compound of Formula (I).

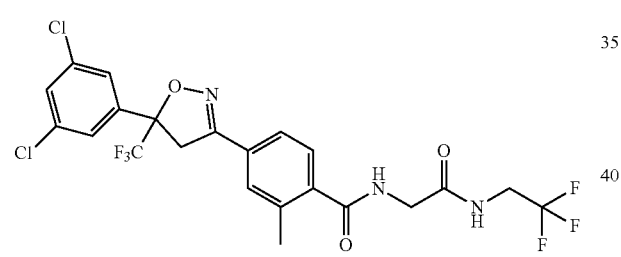

(I)

U.S. Pat. No. 7,662,972 discloses the compound of Formula (I) and synthesis of various isoxazoline-substituted benzamide compounds.

U.S. Pat. Nos. 8,952,175, 9,751,821 and 9,676,692 discloses methods for producing various isoxazoline compounds by reacting a 1,3-bis(substituted phenyl)-3-substituted-2-propen-1-one compound and hydroxylamine in a two-phase system comprising an aliphatic or an aromatic hydrocarbon a solvent which is optionally substituted by a halogen atom, a base and water and by adding an additive selected from a phase-transfer catalyst, a $C_1$-$C_6$ alcohol and an aprotic polar a solvent.

International (PCT) Publication No. WO 2013/021949 discloses methods for producing substituted 4,4-difluoro-2-buten-1-one compounds and substituted isoxazoline compounds by carrying out a dehydration reaction in the presence of a phase transfer catalyst.

The processes described therein are not suitable for an efficient large scale commercial production. Therefore, it is desirable to provide more economical, less hazardous, easy and commercially feasible process for the production of isoxazoline-substituted benzamide compound, Fluralaner of Formula (I).

SUMMARY OF THE INVENTION

In one general aspect, there is provided a process for the preparation of fluralaner, the process comprising:

(a) reacting a compound of Formula (VI) with a compound of Formula (VII),

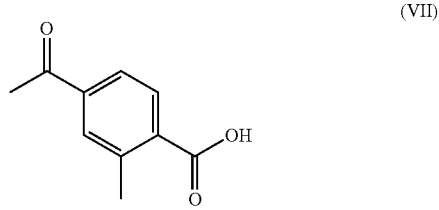

(VII)

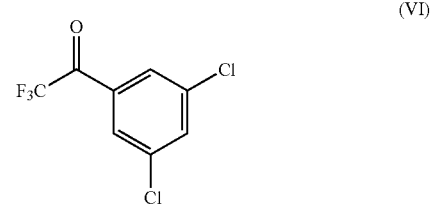

(VI)

to obtain a compound of Formula (V),

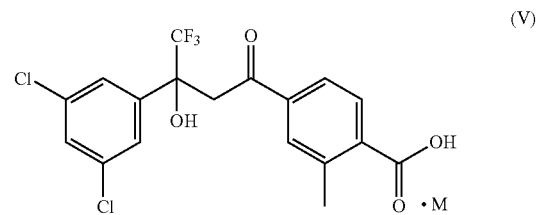

(V)

wherein M is Cs;

(b) converting the compound of Formula (V) into a compound of Formula (IV) or its reactive derivative;

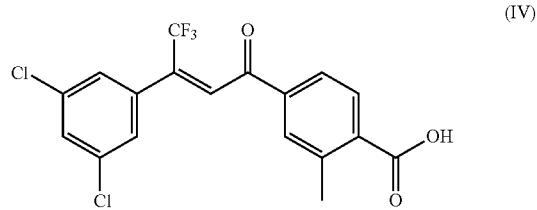 [SMILES: Cc1cc(C(=O)/C=C(/c2cc(Cl)cc(Cl)c2)C(F)(F)F)ccc1C(=O)O]

(IV)

(c) reacting the compound of Formula (IV) or its reactive derivative with 2-amino-N-(2,2,2-trifluoroethyl)acetamide, or salts thereof to obtain a compound of Formula (II); and

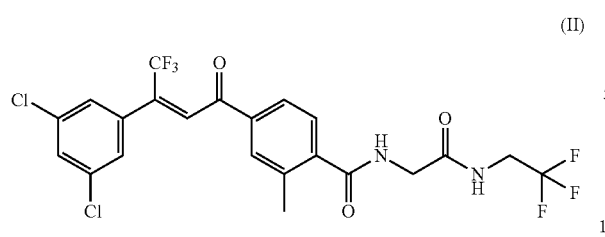

(II)

(d) reacting the compound of Formula (II) with hydroxylamine, or salts thereof to obtain fluralaner.

In another general aspect, there is provided a process for the preparation of fluralaner, the process comprising:

(a) reacting a compound of Formula (IV), or its reactive derivative with 2-amino-N-(2,2,2-trifluoroethyl)acetamide or salts thereof to obtain a compound of Formula (II); and

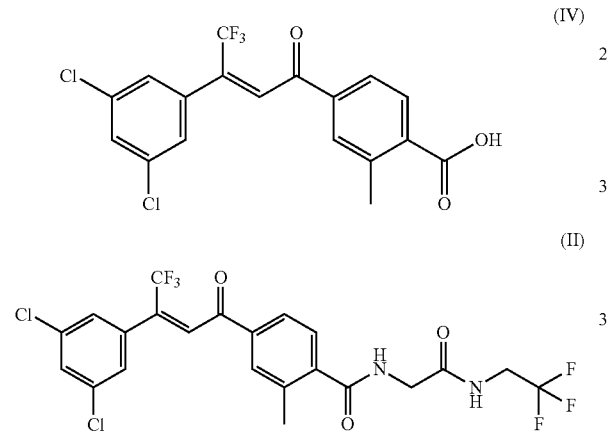

(IV)

(II)

(b) reacting the compound of Formula (II) with hydroxylamine or salts thereof to obtain Fluralaner.

In another general aspect, there is provided an improved process for the preparation of fluralaner, wherein the improvement comprises preparation of fluralaner without isolating the compounds of Formula (IV) and (II).

In another general aspect, there is provided a compound of Formula (V);

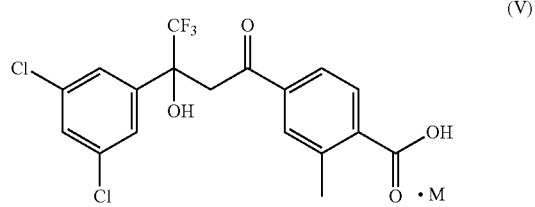

(V)

wherein M is Cs.

In another general aspect, there is provided a process for the preparation of fluralaner, comprising reacting a compound of Formula (X) with 2-Amino-N-(2,2,2-trifluoroethyl)acetamide or salts thereof to obtain fluralaner,

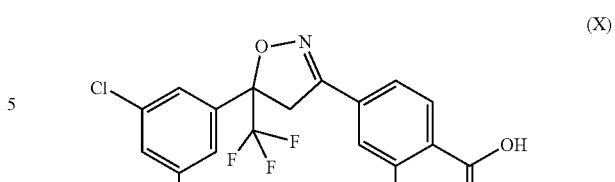

(X)

wherein B is sodium, potassium, cesium, methylamine, ethylamine, n-propylamine, isopropylamine, n-butylamine, isobutylamine, t-butylamine, n-pentylamine, isopentylamine, benzylamine, aniline, dimethlamine, diethylamine, dipropylamine, di-isopropylamine, dibutylamine, diisobutylamine, dipentylamine, diisopentylamine, pyrrolidine, piperidine, piperazine, morpholine, dibenzylamine, tributylamine, tripentylamine, trimethylamine, tripropylamine, tribenzylamine, diisopropylethylamine, or N-methylmorpholine.

In another general aspect, there is provided a compound of Formula (X),

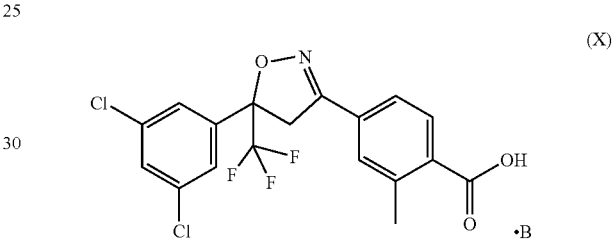

(X)

wherein B is sodium, potassium, cesium, methylamine, ethylamine, n-propylamine, isopropylamine, n-butylamine, isobutylamine, t-butylamine, n-pentylamine, isopentylamine, benzylamine, aniline, dimethlamine, diethylamine, diisopentylamine, pyrrolidine, piperidine, piperazine, morpholine, dibenzylamine, tributylamine, tripentylamine, trimethylamine, tripropylamine, tribenzylamine, diisopropylethylamine, or N-methylmorpholine.

DETAILED DESCRIPTION OF THE INVENTION

The aforementioned general and further specific aspects of the invention are fulfilled by the description of the invention provided herein after.

The terms 'reacting', 'treating' and 'condensing' are generally interchangeable and used in their ordinary meaning as they are in the field of the invention, unless otherwise specifically described.

The terms 'isolating', 'obtaining' and 'purifying' are generally interchangeable and include but not specifically limited to extraction, evaporation, crystallization, filtration, recrystallization or chromatographic operations.

The term 'converting' relates to reacting the compound, to which it refers, with another compound and/or reagent, and/or subjecting it to condition(s) such that it transforms to another compound as results of such process or treatment.

The product(s) obtained may further be purified to obtain them in purer forms.

The product(s) obtained may further be dried additionally to achieve desired level of moisture and/or residual a solvents.

The product(s) obtained may further be converted to any other physical forms thereof which includes but not specifically limited to salt(s), solvate(s), hydrate(s), co-crystal(s) and solid dispersion(s) in either crystalline or amorphous forms.

As used herein, the term "solution" or "reaction mixtures" does not limit to a clear solution only and includes any hazy or opaque mass obtained.

In one general aspect, there is provided a process for the preparation of fluralaner, the process comprising:
(a) reacting a compound of Formula (VI) with a compound of Formula (VII),

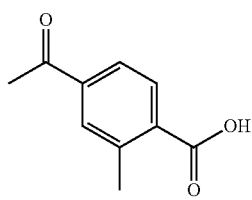
(VII)

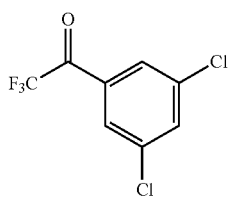
(VI)

to obtain a compound of Formula (V);

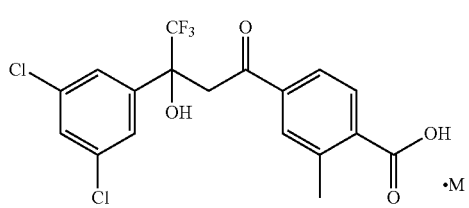
(V)

wherein M is Cs,
(b) converting the compound of Formula (V) into a compound of Formula (IV) or its reactive derivative;

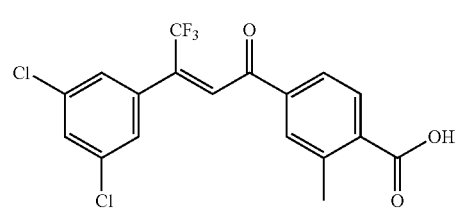
(IV)

(c) reacting the compound of Formula (IV) or its reactive derivative with 2-amino-N-(2,2,2-trifluoroethyl)acetamide or salts thereof to obtain a compound of Formula (II); and

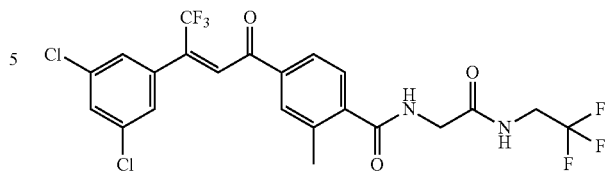
(II)

(d) reacting the compound of Formula (II) with hydroxylamine or salts thereof to obtain fluralaner.

In general, at step (a), 4-acetyl-2-methylbenzoic acid, compound of Formula (VII) can be reacted with 1-(3,5-dichlorophenyl-2,2,2-trifluoroethan-1-one, compound of Formula (VI), in the presence of one or more solvents selected from water, $C_1$-$C_4$-alcohols for example methanol, ethanol, propanol, isopropanol, butanol, 1,4-dioxane, acetonitrile, toluene, dimethyl formamide, or mixtures thereof. Particularly, 1,4-dioxane can be used.

In general, the reaction can be performed in the presence of cesium carbonate as a base to obtain cesium salt of compound of Formula (V).

The reaction can be performed at a temperature arbitrarily from 20° C. to the reflux temperature of the reaction mixtures. Particularly, the reaction can be performed at 60° C. to 75° C.

In general, at step (b), the compound of Formula (V) may be converted into a compound of Formula (IV) by reacting the cesium salt of 4-(3-(3,5-dichlorophenyl)-4,4,4-trifluoro-3-hydroxybutanoyl)-2-methylbenzoic acid with hydrochloric acid in one or more solvents as mentioned herein above and then treating the product with boron trifluoride etherate and acetic anhydride to obtain 4-(3-(3,5-dichlorophenyl)-4,4,4-trifluorobut-2-enoyl)-2-methylbenzoic acid (compound of Formula IV).

The reaction can be carried out at 25 to 120° C. Particularly, at 100 to 120° C.

At step (c), the compound of Formula (IV) directly or its reactive derivative thereof, is reacted with 2-amino-N-(2,2,2-trifluoroethyl)acetamide or salts thereof to obtain a compound of Formula (II). In particular, the reactive derivative may be halide or ester thereof. In general, 2-amino-N-(2,2,2-trifluoroethyl)acetamide or salts thereof can be 2-amino-N-(2,2,2-trifluoroethyl)acetamide hydrochloride or 2-amino-N-(2,2,2-trifluoroethyl)acetamide hydrobromide or 2-amino-N-(2,2,2-trifluoroethyl)acetamide sulfate.

In general, the compound of Formula (IV) can be reacted with 2-amino-N-(2,2,2-trifluoroethyl)acetamide or salts thereof in the presence of a base or a coupling reagent or both in one or more solvents to obtain the compound of Formula (II).

In general, the coupling reagent for the reaction may be selected from N,N'-dicyclohexylcarbodiimide (DCC), 1-ethyl-3-(3-dimethylaminopropyl)-carbodiimide (EDC) or N,N'-diisopropyl carbodiimide (DIC) or their salts, which may be hydrochloride or hydrobromide.

In general, the base for the reaction at step (c) and step (d) may be selected from one or more of alkali metal hydroxides selected from sodium hydroxide, potassium hydroxide, and lithium hydroxide, alkali metal carbonates selected from sodium carbonate, potassium carbonate, lithium carbonate, and cesium carbonate, alkali metal bicarbonate selected from sodium bicarbonate, and potassium bicarbonate, triethylamine, pyridine, N,N-dimethylaminopyridine, 1,8-diazabicyclo-(5.4.0)-7-undecene (DBU), 1,5-diazabicyclo (4.3.0)non-5-ene (DBN), 4-(dimethylamino)pyridine, N,N-dimethylaniline, imidazole, and tributylamine. In particular, the reaction may be performed using N,N-dimethylaminopyridine or triethylamine as a base.

In general, the solvents for the reaction may be selected from one or more of dichlorobenzene, dichloromethane, chloroform, carbon tetrachloride, benzene, toluene, xylene, hexane, heptane, cyclohexane, chlorobenzene, 1,2-dichloroethane, 4-dioxane, ethyl acetate, ethyl propionate, N,N-dimethylformamide, 1,1,1-trichloroethane, trichloroethylene, tetrachloroethylene, diethylether, 1,2-dimethoxyethane, tetrahydrofuran, acetonitrile, and dimethylsulfoxide. Particularly, reaction can be performed in dichloromethane.

The compound of Formula (IV) may be converted into its reactive derivative halide or ester, for example, by reacting with thionyl chloride and dimethyl formamide in hydrocarbon a solvent selected from toluene, benzene, xylene, hexane and heptane to form its halide derivative and then that may be reacted with 2-amino-N-(2,2,2-trifluoroethyl)acetamide or salts thereof in the presence of a base in one or more solvents to obtain the compound of Formula (II).

In general, the solvents for the reaction may be selected from one or more of benzene, toluene, xylene, hexane, heptane, cyclohexane, chlorobenzene, dichlorobenzene, dichloromethane, chloroform, carbon tetrachloride, 1,2-dichloroethane, 1,1,1-trichloroethane, trichloroethylene, tetrachloroethylene, diethylether, 1,2-dimethoxyethane, tetrahydrofuran, 4-dioxane, ethyl acetate, ethyl propionate, N,N-dimethylformamide, N,N-dimethylacetamide, N-methyl-2-pyrrolidone, acetonitrile, and dimethylsulfoxide. Particularly, reaction may be carried out in methylenedichloride or ethyl acetate.

In general, at step (d), 4-(3-(3,5-dichlorophenyl)-4,4,4-trifluorobut-2-enoyl)-2-methyl-N-(2-oxo-2-((2,2,2-trifluoroethyl)amino)ethyl)benzamide (compound of Formula II) is reacted with the hydroxylamine or its salts, in the presence of a base in one or more a solvents to obtain the compound of Formula (I).

The compound of Formula (II) can be reacted with hydroxylamine hydrochloride, hydroxylamine hydrobromide or hydroxylamine sulfate.

In general, the base for the reaction may be selected from one or more of alkali metal hydroxides selected from sodium hydroxide, potassium hydroxide, and lithium hydroxide, alkali metal carbonates selected from sodium carbonate, potassium carbonate, lithium carbonate, and cesium carbonate, alkali metal bicarbonate selected from sodium bicarbonate, and potassium bicarbonate, triethylamine, pyridine, N,N-dimethylaminopyridine, 1,8-diazabicyclo-(5.4.0)-7-undecene (DBU), 1,5-diazabicyclo(4.3.0)non-5-ene (DBN), 4-(dimethylamino)-pyridine, N,N-dimethylaniline, imidazole, and tributylamine. Particularly, sodium hydroxide can be used as the base.

In general, the a solvents for the reaction may be selected from one or more of $C_1$-$C_4$-alcohols selected from methanol, ethanol, propanol, and butanol, benzene, toluene, xylene, hexane, heptane, cyclohexane, diethylether, 1,2-dimethoxyethane, tetrahydrofuran, 1,4-dioxane, ethyl acetate, ethyl propionate, N,N-dimethylformamide, acetonitrile, and dimethylsulfoxide. Particularly, the reaction can be carried out in water, ethanol, tetrahydrofuran, or mixtures thereof.

In another aspect, there is provided a process for the preparation of fluralaner, the process comprising:
  (a) reacting a compound of Formula (IV) or its reactive derivative with 2-amino-N-(2,2,2-trifluoroethyl)acetamide or salts thereof to obtain a compound of Formula (II); and

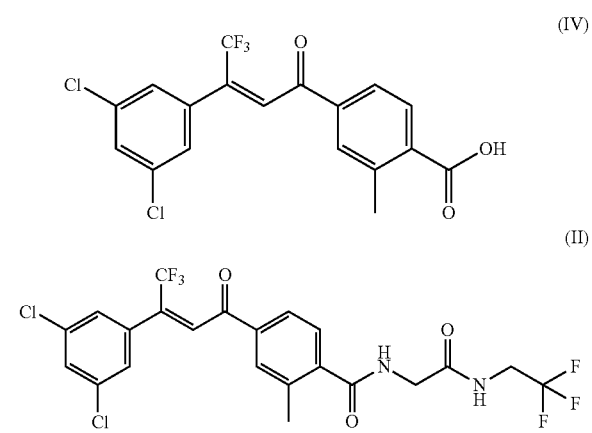

(b) reacting the compound of Formula (II) with hydroxylamine or salts thereof to obtain fluralaner.

In general, at step (a), the compound of Formula (IV) or its reactive derivative are reacted with 2-amino-N-(2,2,2-trifluoroethyl)acetamide or salts thereof, to obtain a compound of Formula (II).

The reactive derivative may be halides or esters thereof.

In general, 2-amino-N-(2,2,2-trifluoroethyl)acetamide or salts thereof may be 2-amino-N-(2,2,2-trifluoroethyl)acetamide hydrochloride, or 2-amino-N-(2,2,2-trifluoroethyl)acetamide hydrobromide, or 2-amino-N-(2,2,2-trifluoroethyl) acetamide hydrobromide sulfate salts.

In general, the compound of Formula (IV) may be reacted with thionyl chloride and dimethyl formamide in hydrocarbon a solvents selected from toluene, benzene, xylene, hexane and heptane to form the reactive derivatives and then that may be reacted with 2-Amino-N-(2,2,2-trifluoroethyl) acetamide hydrochloride in the presence of a base in one or more solvents to obtain the compound of Formula (II).

In general, the base for the reaction can be selected from alkali metal hydroxides, sodium hydroxide, potassium hydroxide, lithium hydroxide; alkali metal carbonates for example sodium carbonate, potassium carbonate, lithium carbonate, cesium carbonate; alkali metal bicarbonate for example sodium bicarbonate; triethylamine, pyridine, 4-(dimethylamino)pyridine, DBU, DBN, N, N-dimethylaniline, imidazole, and tributylamine. Particularly, the reaction may be carried out using triethyl amine as the base.

In general, the a solvents for the reaction may be selected from benzene, toluene, xylene, hexane, heptane, cyclohexane, chlorobenzene, dichlorobenzene, dichloromethane, chloroform, carbon tetrachloride, 1,2-dichloroethane, 1,1,1-trichloroethane, trichloroethylene, tetrachloroethylene, diethylether, 1,2-dimethoxyethane, tetrahydrofuran, 4-dioxane, ethyl acetate, ethyl propionate, N,N-dimethylformamide, N,N-dimethylacetamide, N-methyl-2-pyrrolidone, acetonitrile, and dimethylsulfoxide. The reaction can be carried out in ethyl acetate or dichloromethane.

In general, the reaction can be performed at −5 to 50° C. Particularly, at 0 to 20° C.

In general, at step (b), 4-(3-(3,5-Dichlorophenyl)-4,4,4-trifluorobut-2-enoyl)-2-methyl-N-(2-oxo-2-((2,2,2-trifluoroethyl)amino)ethyl)benzamide, (compound of Formula II) is reacted with hydroxylamine or salts thereof in the presence of a base in one or more solvents to obtain the compound of Formula (I).

The compound of Formula (II) may be reacted with hydroxylamine hydrochloride, hydroxylamine hydrobromide or hydroxylamine sulfate.

In general, the base for the said reaction may be selected from sodium hydroxide, potassium hydroxide, lithium hydroxide, sodium carbonate, potassium carbonate, lithium carbonate, cesium carbonate, sodium bicarbonate, triethylamine, pyridine, 4-(dimethylamino)pyridine, DBU, DBN, N,N-dimethylaniline, imidazole and tributylamine. Particularly, sodium hydroxide may be selected as the base.

In general, the solvents for the reaction may be selected from water, $C_1$-$C_4$ alcohols for example methanol, ethanol, propanol, and butanol, benzene, toluene, xylene, hexane, heptane, cyclohexane, diethylether, 1,2-dimethoxyethane, tetrahydrofuran, 1,4-dioxane, ethyl acetate, ethyl propionate, N,N-dimethylformamide, acetonitrile, and dimethylsulfoxide or mixtures thereof. Particularly, reaction may be performed in ethanol, water or tetrahydrofuran, or mixtures thereof.

In another general aspect, there is provided an improved process for the preparation of fluralaner, wherein the process comprises preparation of fluralaner without isolating the compounds of Formula (IV) and (II).

In another general aspect, there is provided a compound of Formula (V),

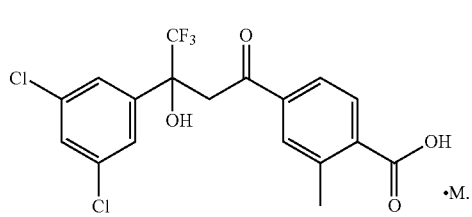

wherein M is Cs.

In another general aspect, there is provided a compound of Formula (X),

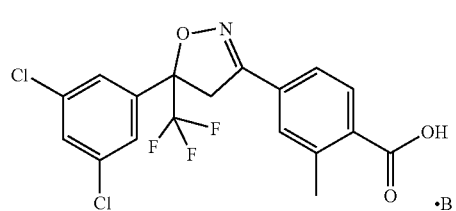

wherein B is sodium, potassium, cesium, methylamine, ethylamine, n-propylamine, isopropylamine, n-butylamine, isobutylamine, t-butylamine, n-pentylamine, isopentylamine, benzylamine, aniline, dimethlamine, diethylamine, diisopentylamine, pyrrolidine, piperidine, piperazine, morpholine, dibenzylamine, tributylamine, tripentylamine, trimethylamine, tripropylamine, tribenzylamine, diisopropylethylamine, or N-methylmorpholine.

In another general aspect, there is provided a process for the preparation of a compound of Formula (X), comprising reacting 4-(3-(3,5-Dichlorophenyl)-4,4,4-trifluorobut-2-enoyl)-2-methylbenzoic acid with hydroxyl amine or its salts.

The reaction can be performed in the presence of a base in one or more solvents.

In general, the base for the reaction can be selected from sodium hydroxide, potassium hydroxide, cesium hydroxide, methylamine, ethylamine, n-propylamine, isopropylamine, n-butylamine, isobutylamine, t-butylamine, n-pentylamine, isopentylamine, benzylamine, aniline, dimethlamine, diethylamine, dipropylamine, diisopropylamine, dibutylamine, diisobutylamine, dipentylamine, diisopentylamine, pyrrolidine, piperidine, piperazine, morpholine, dibenzylamine, tripentylamine, trimethylamine, tripropylamine, tributylamine, tribenzylamine, diisopropylethylamine, or N-methyl morpholine.

In general, the reaction can be carried out at 0 to 50° C. Particularly, at 5 to 15° C.

In general, the reaction can be performed in one or more a solvent selected from water, $C_1$-$C_4$alcohols selected from methanol, ethanol, propanol, and butanol, benzene, toluene, xylene, hexane, heptane, cyclohexane, diethylether, 1,2-dimethoxyethane, tetrahydrofuran, 1,4-dioxane, ethyl acetate, ethyl propionate, N,N-dimethylformamide, acetonitrile, and dimethylsulfoxide. Particularly, the reaction can be performed in ethanol and water.

In another general aspect, there is provided a process for the preparation of fluralaner, comprising reacting a compound of Formula (X) with 2-Amino-N-(2,2,2-trifluoroethyl)acetamide or salts thereof to obtain fluralaner.

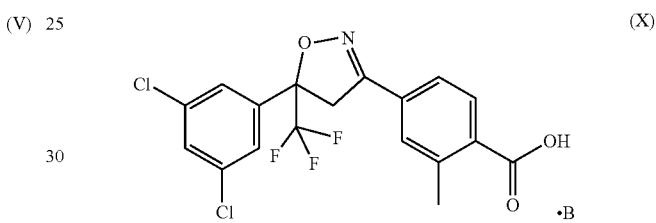

wherein B is sodium, potassium, cesium, methylamine, ethylamine, n-propylamine, isopropylamine, n-butylamine, isobutylamine, t-butylamine, n-pentylamine, isopentylamine, benzylamine, aniline, dimethlamine, diethylamine, dipropylamine, di-isopropylamine, dibutylamine, diisobutylamine, dipentylamine, diisopentylamine, pyrrolidine, piperidine, piperazine, morpholine, dibenzylamine, tributylamine, tripentylamine, trimethylamine, tripropylamine, tribenzylamine, diisopropylethylamine, or N-methylmorpholine.

The reaction can be performed using either 2-Amino-N-(2,2,2-trifluoroethyl)acetamide or its salts selected from hydrochloride, hydrobromide or hydroiodide salt. Preferably hydrochloride salt.

During the reaction, the compound of Formula (X) can be dissolved in one or more solvent and its pH is adjusted between 2 to 3 using hydrochloric acid. Then the compound can be extracted in a solvent as mentioned herein below. The compound can be reacted with thionyl chloride and N, N-dimethyl formamide and then further can be reacted with 2-Amino-N-(2,2,2-trifluoroethyl)acetamide hydrochloride in solvent as mentioned herein below to obtain the compound of Formula (I).

The reaction can be performed in one or more solvent selected from toluene, benzene, xylene, dichloromethane, dichloroethane, ethyl acetate, N, N-dimethyl formamide or mixture thereof.

In general, the reaction with 2-Amino-N-(2,2,2-trifluoroethyl)acetamide hydrochloride can be performed at 5 to 100° C. Particularly, at 10° C. to 20° C.

In another general aspect, there is provided a process for the preparation of Fluralaner, substantially as same as that depicted in Scheme-I.

Scheme-I

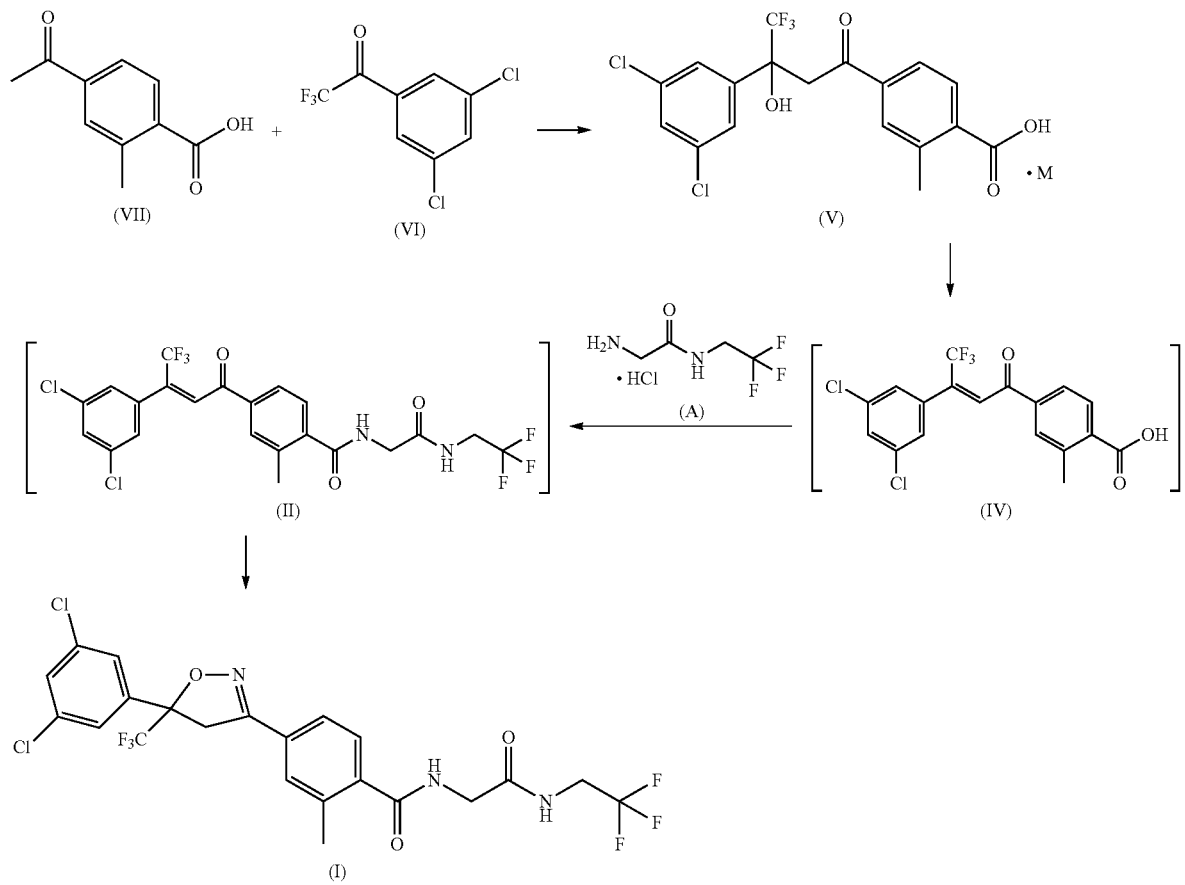

wherein M is Cs.

The examples are set forth to aid in understanding the invention but are not intended to, and should not be construed to limit its scope in any way. The examples do not include detailed descriptions of conventional methods. Such methods are well known to those of ordinary skill in the art and are described in various publications.

EXAMPLES

Example 1: Preparation of 4-[5-(3,5-dichlorophenyl)-4,5-dihydro-5-(trifluoro methyl)-3-isoxazolyl]-2-methyl-N-[2-oxo-2-[(2,2,2-trifluoroethyl) amino] ethyl]benzamide (compound of Formula I)

Stage-1: Preparation of 4-(3-(3,5-dichlorophenyl)-4, 4,4-trifluoro-3-hydroxybutanoyl)-2-methylbenzoic acid cesium (compound of Formula V)

In a round bottom flask, a solution of 10 g 4-Acetyl-2-methylbenzoic acid in 100 mL 1,4-Dioxane and 22.80 g cesium carbonate were added and stirred for 15 to 30 minutes. 17.04 g 1-(3,5-dichlorophenyl-2,2,2-trifluoro-ethan-1-one was added and the reaction mass was stirred at 70 to 75° C. for 20 hours. After the completion of the reaction, it was cooled to 25 to 35° C. and filtered, washed with 20 mL 1,4-Dioxane. The solid was dried for 6 hours at 50 to 55° C. to obtain cesium salt of 4-(3-(3,5-Dichlorophenyl)-4,4,4-trifluoro-3-hydroxybutanoyl)-2-methylbenzoic acid, compound of Formula (V).

Stage-2: Preparation of 4-(3-(3,5-dichlorophenyl)-4, 4,4-trifluorobut-2-enoyl)-2-methylbenzoic acid (compound of Formula IV)

In a round bottom flask, compound of Formula (V) obtained from the stage-1, 96 mL ethyl acetate and 96 mL water were added and pH was adjusted to 1.50 to 2.0 with 50% w/w dil HCl. After the layers were separated, the ethyl acetate layer was washed water and sodium sulphate, ethyl acetate was removed via distillation. In the obtained residue, 60 mL toluene was added and stirred for 10 to 15 minutes at 60 to 65° C. The reaction mixture was cooled at 25 to 35° C., stirred and filtered. The wet-cake was washed with toluene and then dried at 55 to 60° C. for 6 hours to obtain 4-(3-(3,5-Dichlorophenyl)-4,4,4-trifluoro-3-hydroxybutanoyl)-2-methylbenzoic acid. In an another flask, a solution of 13 g 4-(3-(3,5-Dichlorophenyl)-4,4,4-trifluoro-3-hydroxybutanoyl)-2-methylbenzoic acid in 65 mL toluene and 5.50 g boron trifluoride etherate were added and then 4.70 g acetic anhydride was added into the reaction mixtures at 60 to 65° C. The reaction mixtures was stirred at 105 to 115° C. for 2 hours. After the completion of the reaction, unreacted 4-(3-(3,5-Dichlorophenyl)-4,4,4-trifluoro-3-hydroxybutanoyl)-2-methylbenzoic acid was observed 0.50% w/w, the reaction mixtures was cooled to 25 to 35° C. and 65 mL toluene and 65 mL water were added. The layers were separated and the toluene layer was washed with water and after sodium sulphate treatment, was distilled to obtain 4-(3-(3,5-dichlorophenyl)-4,4,4-trifluorobut-2-enoyl)-2-methylbenzoic acid (compound of Formula IV). Yield: 88.54%.

Stage-3: Preparation of 4-(3-(3,5-Dichlorophenyl)-4,4,4-trifluorobut-2-enoyl)-2-methyl-N-(2-oxo-2-((2,2,2-trifluoroethyl)amino)ethyl)benzamide (compound of Formula II)

In a round bottom flask, a solution of 11 g 4-(3-(3,5-Dichlorophenyl)-4,4,4-trifluorobut-2-enoyl)-2-methylbenzoic acid in 110 mL toluene and 8.10 g thionyl chloride and 0.5 g dimethyl formamide were added and stirred at 85 to 90° C. for 2 hours. The solvent was distilled out under vacuum and stripped with 11 mL toluene. 55 mL toluene was added into the reaction mixtures and stored separately. In another flask, 6.80 g 2-Amino-N-(2,2,2-trifluoroethyl)acetamide hydrochloride and 9.60 g Triethyl amine in 110 mL ethyl acetate was taken and the above solution was added under nitrogen atmosphere at 10 to 20° C. and stirred for 2 hours. 55 mL water was added into the reaction mixtures at 25 to 35° C. and stirred. The separated organic layer was washed with water and after sodium sulphate treatment, was distilled to obtain 4-(3-(3,5-dichlorophenyl)-4,4,4-trifluorobut-2-enoyl)-2-methyl-N-(2-oxo-2-((2,2,2-trifluoroethyl)amino)ethyl)-benzamide (compound of Formula-II). Yield: 98.71%.

Stage-4: Preparation of 4-(3-(3,5-dichlorophenyl)-4,4,4-trifluorobut-2-enoyl)-2-methyl-N-(2-oxo-2-((2,2,2-trifluoroethyl)amino)ethyl)benzamide (compound of Formula II) (Method-II)

In a round bottom flask, a solution of 1 g 4-(3-(3,5-Dichlorophenyl)-4,4,4-trifluorobut-2-enoyl)-2-methylbenzoic acid in 10 mL methylene dichloride, 0.076 g N,N-dimethylamino pyridine, 0.53 g 2-Amino-N-(2,2,2-trifluoroethyl)acetamide hydrochloride and 0.30 gm triethylamine were taken and the reaction mixtures was stirred at 25 to 35° C. The reaction mixtures was cooled to 0 to 10° C. and 0.53 g N-(3-Dimethylaminopropyl)-N'-ethylcarbodiimide hydrochloride (EDC-HCl) was added and stirred for 12 hours at 25 to 35° C. After completion of the reaction, the reaction mixtures was washed with citric acid solution. The organic layer was treated with sodium sulphate and the solvent was removed by distillation. 2.1 mL ethyl acetate and 4.1 mL n-hexane were added into the reaction mixtures at 60 to 65° C. and cooled to 25 to 35° C. The reaction mixture was stirred for 30 to 45 minutes at 25 to 35° C., filtered and washed with mixture of 0.60 mL ethyl acetate and 1.40 mL n-hexane. The solid was dried at 55 to 60 °C for 6 hours to obtain 4-(3-(3,5-Dichlorophenyl)-4,4,4-trifluorobut-2-enoyl)-2-methyl-N-(2-oxo-2-((2,2,2-trifluoroethyl)amino)ethyl) benzamide.

Stage-5: Preparation of 4-[5-(3,5-Dichlorophenyl)-4,5-dihydro-5-(trifluoromethyl)-3-isoxazolyl]-2-methyl-N-[2-oxo-2-[(2,2,2-trifluoroethyl) amino] ethyl] benzamide (compound of Formula I)

In a round bottom flask, a solution of 4 g 4-(3-(3,5-Dichlorophenyl)-4,4,4-trifluorobut-2-enoyl)-2-methyl-N-(2-oxo-2-((2,2,2-trifluoroethyl)amino)ethyl) benzamide in 28 mL ethanol and a solution of 1.20 g sodium hydroxide in 4 mL water were added and stirred at 5 to 15° C. A solution of 0.91 g hydroxylamine sulfate in 3 mL water was added and stirred at 5 to 15° C. for 2 hour. After completion of the reaction, the solvent was removed by distillation under vacuum. 40 mL ethyl acetate and 20 mL water was added into the reaction mixture and the reaction mixture was stirred. The pH of the reaction mixtures was adjusted to 6.0 to 6.5 using 50% hydrochloride acid solution. The separated organic layer was washed with 20 mL water followed by 12 mL 10% sodium chloride solution. The organic layer was treated with sodium sulphate and the solvent was removed by distillation. 12 mL ethyl acetate and 24 mL n-hexane were added into the reaction mixture at 60 to 65° C. and cooled to 25 to 35° C. The reaction mixtures was stirred for 30 to 45 minutes at 25 to 35° C. and filtered and washed with a mixture of 2 mL ethyl acetate and 4 mL n-hexane. The solid was dried at 55 to 60° C. for 6 hours to obtain 4-[5-(3,5-Dichlorophenyl)-4,5-dihydro-5-(trifluoromethyl)-3-isoxazolyl]-2-methyl-N-[2-oxo-2-[(2,2,2-trifluoroethyl)amino]ethyl]benzamide (compound of Formula I).

Example 2: Preparation of sodium 4-(5-(3,5-Dichlorophenyl)-5-(trifluoromethyl)-4,5-dihydroisoxazol-3-yl)-2-methylbenzoate (compound of Formula X)

In a round bottom flask, a solution of 10 g 4-(3-(3,5-Dichlorophenyl)-4,4,4-trifluorobut-2-enoyl)-2-methylbenzoic acid (compound of Formula IV) in 70 mL ethanol and 4.0 g sodium hydroxide solution in 10 mL water were stirred at 5 to 15° C. and 3.05 g hydroxyl amine sulfate solution in 7 mL water was added and the reaction mixture was stirred at 5 to 15° C. for 2 hour. After the completion of the reaction, the reaction mixture was heated to 55° C. and solvent was removed by distillation under vacuum. The reaction mixture was cooled to 25 to 35° C. and 180 mL water was added and stirred for 30 to 45 minutes at 25 to 35° C. and then filtered and washed with 20 mL water. The solid was dried at 55 to 60° C. for 6 hours to obtain sodium 4-(5-(3,5-Dichlorophenyl)-5-(trifluoromethyl)-4,5-dihydroisoxazol-3-yl)-2-methylbenzoate (compound of Formula X-sodium salt).

Example 3: Preparation of 4-[5-(3,5-dichlorophenyl)-4,5-dihydro-5-(trifluoro methyl)-3-isoxazolyl]-2-methyl-N-[2-oxo-2-[(2,2,2-trifluoroethyl) amino] ethyl]benzamide (compound of Formula I)

Stage-1: Preparation of 4-(3-(3,5-dichlorophenyl)-4,4,4-trifluoro-3-hydroxybutanoyl)-2-methylbenzoic acid cesium salt (compound of Formula V)

In a round bottom flask, 35 mL water was taken and 228.5 g cesium carbonate was added lotwise. The reaction mixtures was stirred at 25 to 35° C. for 10 to 15 minutes. 100 g 4-acetyl-2-methylbenzoic acid was added and stirred at 25 to 35° C. for 20 to 25 minutes. 170.5 g 1-(3,5-Dichlorophenyl-2,2,2-trifluoroethan-1-one was added at 25 to 35° C. and stirred. The reaction mixtures was then stirred at 65 to 70° C. to 12 to 13 hours. After complying of HPLC results, the reaction mixtures was cooled to 25 to 35° C. and 250 mL of 1,4-dioxane was added and stirred for 20 to 30 minutes. The solid was filtered and washed with 1,4-dioxane and dried under vacuum to obtain a dried solid. The solid was taken in another round bottom flask, and 1200 mL water was added. The reaction mixtures was stirred for 50 minutes to an hour at 25 to 35° C. then it was filtered and the solid was washed with water and dried under vacuum to obtain cesium salt of 4-(3-(3,5-Dichlorophenyl)-4,4,4-trifluoro-3-hydroxybutanoyl)-2-methylbenzoic acid, compound of Formula (V).

Stage-2: 4-(3-(3,5-Dichlorophenyl)-4,4,4-trifluorobut-2-enoyl)-2-methyl-N-(2-oxo-2-((2,2,2-trifluoroethyl)amino)ethyl)benzamide (compound of Formula-II)

In a round bottom flask, 100 g of compound of Formula (V) was taken in 300 mL ethyl acetate and stirred for 10 to 15 minutes at 25-35° C. 300 mL water was added and stirred. The pH of the reaction mixtures was adjusted between 1.5 to 2.5 using diluted HCl solution and stirred for 25 to 30 minutes. The separated ethyl acetate layer was washed with water and distilled under vacuum. 25 mL toluene was added at below 65° C. and stirred. Toluene was distilled below 65° C. under vacuum and again 375 mL toluene was added and stirred for 10 to 15 minutes at 25-35° C. 12.91 g Boron trifluoride etherate was added under nitrogen atmosphere and stirred for 10 to 15 minutes at 25-35° C. 31.44 g acetic anhydride was added and then the reaction mixtures was stirred for 3 to 4 hours at 105-115° C. The reaction mixtures was then cooled to 25-35° C. and 4.5 g acetic anhydride was added under nitrogen atmosphere. The reaction mixtures was stirred at 105-115° C. for 2 hours. After completion of the reaction, the reaction mixtures was cooled and 375 mL water was added and stirred. The layers were separated. The organic layer was taken in an another flask and toluene was distilled our under vacuum at below 65° C. 71.40 g thionyl chloride and 3 mL DMF were added into the reaction mixtures at below 65° C. and stirred for 10 to 15 minutes at 25-35° C. and then 3 to 4 hours at 65-75° C. 75 mL dichloromethane was added and stirred for 10 to 15 minutes at 25-35° C., then it was distilled out to obtain chloride derivative of compound (IV). Again 365 mL dichloromethane was added and the reaction mixtures was cooled to 0-10° C. and 40 g 2-Amino-N-(2,2,2-trifluoroethyl)acetamide HCl and 40 g triethyl amine were added and the reaction mixtures was stirred for an hour at 0-10° C. and then 10-15 minutes at 28-35° C. 365 mL dichloromethane and 220 mL water were added and stirred for 10 to 15 minutes at 28-35° C. Layers were separated and the dichloromethane layer containing the product was washed with water and then dichloromethane was distilled out under vacuum at below 60° C. 90 mL isopropyl alcohol was added into the reaction mixture and stirred for 10 to 15 minutes at below 60° C. and distilled. 450 mL isopropyl alcohol was added at below 45° C. and the reaction mixture was stirred for 10 to 20 minutes at 69-70° C. The reaction mixture was then cooled. The solid obtained was filtered and washed with isopropyl alcohol and dried under vacuum for 6 hours±15 min (Above 700 mm/Hg) at 60 to 70° C. to obtain the compound of Formula (II).

Stage-3: Preparation of 4-[5-(3,5-Dichlorophenyl)-4,5-dihydro-5-(trifluoromethyl)-3-isoxazolyl]-2-methyl-N-[2-oxo-2-[(2,2,2-trifluoroethyl) amino] ethyl] benzamide (compound of Formula I)

In a round bottom flask, 300 mL water and 18.0 g Hydroxylamine hydrochloride were added and stirred for 15 to 20 minutes at 25 to 35° C. and then sodium hydroxide solution (18.50 g sodium hydroxide in 90 mL water) was added into the reaction mixtures and stirred for 20 to 25 minutes at 25 to 35° C. A solution of 100 g compound of Formula (II) in 275 mL tetrahydrofuran was added and the reaction mixtures was stirred for 4 hours to 5 hours at 25 to 35° C. After completion of the reaction, tetrahydrofuran was distilled under vacuum at below 55° C. The reaction mixtures was cooled to 25 to 35° C. and 400 mL ethyl acetate was added and stirred for 10 to 20 minutes, then 300 mL water was added and stirred for 10 to 20 minutes. The pH of the reaction mixtures was adjusted between 5.0 to 6.5 using diluted HCl solution and then the layers were separated. The ethyl acetate layer was filtered and the a solvent was distilled out under vacuum till one to two volume reaction mass remains below 60° C. and again 300 mL ethyl acetate was added and the a solvent was distilled out under vacuum till two to three volume reaction mass remains below 60° C. and stirred for 5 to 10 minutes. 350 mL n-heptane was added into the reaction mixtures at 65 to 75° C. and stirred at this temperature for 10 to 15 minutes. The reaction mixtures was then cooled and stirred to 1 to 2 hours at 25 to 35° C. and then filtered and washed with ethyl acetate and n-heptane and dried to obtain a wet cake. The wet cake was taken in an another flask and 175 mL ethyl acetate was added and stirred for 15 to 20 minutes at 65 to 75° C. then it was cooled and stirred at 25 to 35° C. for one to two hours and then filtered and washed with ethyl acetate and n-heptane and the solid was dried in vacuum tray dryer for 6 hours±15 minutes (NLT 700 mm Hg) at 60 to 70° C. to obtain compound of Formula (I).

Example 4: Preparation of 4-[5-(3,5-dichlorophenyl)-4,5-dihydro-5-(trifluoro methyl)-3-isoxazolyl]-2-methyl-N-[2-oxo-2-[(2,2,2-trifluoroethyl) amino] ethyl]benzamide (compound of Formula I)

In a round bottom flask, a solution of 4.40 g sodium 4-(5-(3,5-Dichlorophenyl)-5-(trifluoro methyl)-4,5-dihydroisoxazol-3-yl)-2-methylbenzoate in 22 mL ethyl acetate was added and pH was adjusted between 2 to 3 using hydrochloric acid solution. The layers were separated and the organic layer was washed using water and then by sodium chloride solution. The solvent was removed to obtain a residue. In an another flask, a solution of this residue in 40 mL toluene was added and 5.0 g thionyl chloride and 0.5 g dimethyl formamide were added and stirred at 85 to 95° C. for 3 hours. The solvent was distilled out under vacuum and 40 mL toluene was added into the reaction mixture and kept aside. In another flask, 4.80 g 2-Amino-N-(2,2,2-trifluoroethyl)acetamide hydrochloride and 6.8 g triethyl amine in 80 mL ethyl acetate was taken and the above solution in toluene was added under nitrogen atmosphere at 10 to 20° C. and stirred for 2 hours. After completion of the reaction, 55 mL water was added into the reaction mixture at 25 to 35° C. and stirred. Layers were separated and the organic layer was washed with water and sodium sulphate solution. The solvent from the organic layer was removed by distillation and 32 mL ethyl acetate and 64 mL n-hexane were added into the reaction mixture at 60 to 70° C. and cooled to 25 to 35° C. The reaction mixture was stirred for 30 to 45 minutes at 25 to 35° C. and then the solid was filtered, and washed with a mixture of 6.2 mL ethyl acetate and 9.8 mL n-hexane. The solid was dried at 50 to 60° C. for 14 hours to obtain 4-[5-(3,5-dichlorophenyl)-4,5-dihydro-5-(trifluoromethyl)-3-isoxazolyl]-2-methyl-N-[2-oxo-2-[(2,2,2-trifluoroethyl)amino]ethyl]benzamide (compound of Formula I). Yield: 80.72%.

While the present invention has been described in terms of its specific embodiments, certain modifications and equivalents will be apparent to those skilled in the art and are intended to be included within the scope of the present invention.

The invention claimed is:
1. A process for the preparation of fluralaner, the process comprising:
(a) reacting a compound of Formula (VI) with a compound of Formula (VII),

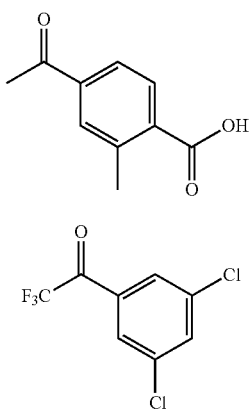

to obtain a compound of Formula (V),

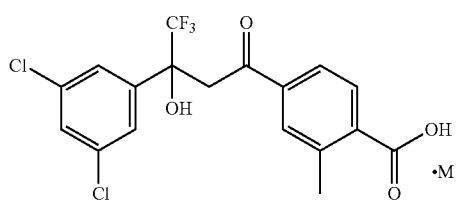

wherein M is Cs,
wherein the reaction is performed in the presence of cesium carbonate;
(b) converting the compound of Formula (V) into a compound of Formula (IV) or its reactive derivative,

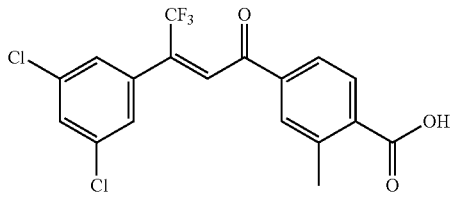

wherein the reaction is performed in the presence of boron trifluoride etherate and acetic anhydride;
(c) reacting the compound of Formula (IV) or its reactive derivative with 2-Amino-N-(2,2,2-trifluoroethyl)acetamide, or salts thereof to obtain a compound of Formula (II); and

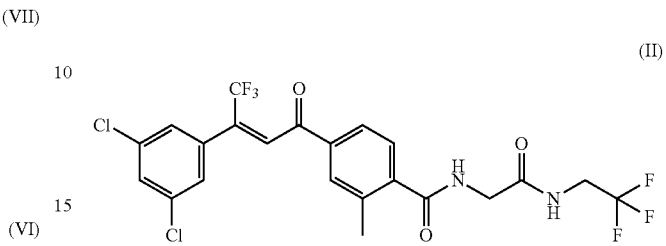

(d) reacting the compound of Formula (II) with hydroxylamine, or salts thereof to obtain fluralaner.

2. The process according to claim 1, wherein the reaction at step (a) is performed in the presence of water, $C_1$-$C_4$-alcohols, 1,4-dioxane, acetonitrile, toluene, dimethyl formamide, or mixtures thereof.

3. The process according to claim 1, wherein the reaction at step (c) is performed in the presence of a coupling reagent selected from N,N'-dicyclohexylcarbodiimide (DCC), 1-ethyl-3-(3-dimethylaminopropyl)carbodiimide (EDC) or N,N'-diisopropylcarbodiimide (DIC).

4. The process according to claim 1, wherein the reactions at step (c) and step (d) are performed in the presence of a base comprises one or more of alkali metal hydroxides selected from sodium hydroxide, potassium hydroxide, and lithium hydroxide, alkali metal carbonates selected from sodium carbonate, potassium carbonate, lithium carbonate, and cesium carbonate, alkali metal bicarbonate selected from sodium bicarbonate, and potassium bicarbonate, triethylamine, pyridine, N,N-dimethyl aminopyridine, 1,8-diazabicyclo-(5.4.0)-7-undecene (DBU), 1,5-diazabicyclo(4.3.0)non-5-ene (DBN), 4-(dimethylamino)pyridine, N,N-dimethylaniline, imidazole, and tributylamine.

5. The process according to claim 1, wherein the reaction at step (d) is performed in the presence of a solvent selected from methanol, ethanol, propanol, and butanol, benzene, toluene, xylene, hexane, heptane, cyclohexane, diethylether, 1,2-dimethoxyethane, tetrahydrofuran, 1,4-dioxane, ethyl acetate, ethyl propionate, N,N-dimethylformamide, acetonitrile, and dimethylsulfoxide.

6. The process according to claim 1, wherein the process comprises preparation of fluralaner without isolating the compounds of Formula (IV) and (II).

* * * * *